United States Patent
Gendreau et al.

(10) Patent No.: US 10,393,682 B2
(45) Date of Patent: Aug. 27, 2019

(54) MULTIPLEXING X-RAY FLUORESCENCE SYSTEM AND METHOD

(71) Applicant: U.S.A. as represented by the Administrator of the National Aeronautics and Space Administration, Washington, DC (US)

(72) Inventors: Keith C. Gendreau, Greenbelt, MD (US); Zaven Arzoumanian, Greenbelt, MD (US); Robert G. Baker, Berlin, MD (US); Norman Dobson, Greenbelt, MD (US); Richard Koenecke, Greensboro, MD (US)

(73) Assignee: U.S.A. as represented by the Administrator of the National Aeronautics and Space Administration, Washington, DC (US)

( * ) Notice: Subject to any disclaimer, the term of this patent is extended or adjusted under 35 U.S.C. 154(b) by 774 days.

(21) Appl. No.: 14/858,399

(22) Filed: Sep. 18, 2015

(65) Prior Publication Data

US 2017/0082562 A1    Mar. 23, 2017

(51) Int. Cl.
*G01N 23/223* (2006.01)

(52) U.S. Cl.
CPC ..... *G01N 23/223* (2013.01); *G01N 2223/076* (2013.01); *G01N 2223/206* (2013.01); *G01N 2223/507* (2013.01); *G01N 2223/643* (2013.01)

(58) Field of Classification Search
CPC .......... G01N 23/223; G01N 2223/076; G01N 2223/507
See application file for complete search history.

(56) References Cited

U.S. PATENT DOCUMENTS

| | | | | |
|---|---|---|---|---|
| 4,048,496 A * | 9/1977 | Albert | .................. | G01N 23/223 378/113 |
| 5,545,900 A * | 8/1996 | Bolk | ......................... | G01T 1/17 250/395 |
| 9,117,622 B2 * | 8/2015 | Gendreau | ............. | H01J 35/065 |
| 2003/0128804 A1* | 7/2003 | Poteet | .................. | G01N 23/223 378/44 |
| 2005/0232392 A1* | 10/2005 | Bradley | ............... | G01N 23/223 378/45 |
| 2013/0022167 A1* | 1/2013 | Cardoso | ............. | G01N 23/2206 378/46 |
| 2014/0044239 A1* | 2/2014 | Gendreau | ............. | H01J 35/065 378/123 |
| 2017/0082562 A1* | 3/2017 | Gendreau | ............ | G01N 23/223 |

\* cited by examiner

*Primary Examiner* — Thomas R Artman
(74) *Attorney, Agent, or Firm* — Heather Goo; Bryan A. Geurts; Mark P. Dvorscak (57) ABSTRACT

A multiplexing x-ray fluorescence (MXRF) system and method are provided. The system can include a simple detector that counts x-rays with time resolution. A time-variable applied radiation source is used. The MXRF applied radiation source can produce an excitation spectrum with a peak average energy that grows with time and then recycles. Elemental identification can be achieved by time-correlating x-ray counts detected by the detector, with the time-variable applied radiation field. The system and method provide design flexibility for both commercial and NASA applications.

20 Claims, 7 Drawing Sheets

MULTIPLEXING X-RAY FLUORESCENCE SYSTEM AND METHOD

STATEMENT REGARDING FEDERALLY SPONSORED RESEARCH OR DEVELOPMENT

The invention described herein was made in part by employees of the United States Government and may be manufactured and used by or for the Government of the United States of America for governmental purposes without the payment of any royalties thereon or therefore.

FIELD OF THE INVENTION

The present invention relates to an x-ray fluorescence system and method.

BACKGROUND OF THE INVENTION

X-ray fluorescence (XRF) is a common technique used to identify the elemental composition of a sample. XRF is used in a variety of fields ranging from mining, to artwork analysis, to crime scene investigations, to planetary exploration. In traditional XRF, Energy Dispersive (ED) detectors are used to identify characteristic spectral line emission excited in a sample by an applied radiation source.

XRF uses the energy-dispersed identification of characteristic x-ray emission lines from elements that are excited by applied x-rays or high-energy particles; this applied radiation typically has a fixed spectrum that spans energies high enough to excite emission from a broad range of characteristic lines. An ED detector then uses its energy-resolving capability to identify the lines and thus the constituent elements. ED detectors with adequate energy resolution are typically small (<1 cm across) and must be in close proximity to the excited sample in order to preserve sensitivity. The characteristic photons disperse in random directions from the excited atom; to capture the characteristic photons, the small ED detector must be placed close to a sample to capture a large solid-angle, and more photons. Typical distances are comparable to the ED detector size, in the range of millimeters, or nearly in contact.

ED detectors are limited to small sizes for a number of reasons. Typically, ED detectors are silicon devices that are cooled to reduce thermal noise and increase energy resolution. Power requirements to cool large detectors can become complex and costly. Also, the fabrication of large, high quality, energy resolving detectors can be expensive due to the high purity of material required. Thus, larger ED detectors are costly and practically limited by power and availability.

NASA has identified resource identification and utilization as a means of supporting human exploration of the Moon, asteroids, Mars, and other Solar System bodies. Mars rover missions carry XRF units that use radioactive alpha-particle sources to stimulate XRF from samples encountered along their traverses. Commercial handheld units for use on Earth also exist. Both require near-contact for measurements for the reasons outlined above. For fine-scale mapping of extraterrestrial mineral resources, for example, astronauts would have to stop and exit their vehicles every few feet or so to make a contact-XRF measurement to map elemental composition, and resource extraction would go very slowly. Such exploration could benefit from a new XRF detection technique that does not require close proximity to a sample in order to determine its composition.

SUMMARY OF THE INVENTION

According to various embodiments of the present invention, a multiplexing x-ray fluorescence (MXRF) system and method are provided. The system can comprise a simple detector and counts x-ray photons with time resolution. A time-variable applied radiation source is used that supplies a plurality of x-rays of different respective energies. In some embodiments, the MXRF applied radiation source produces an excitation spectrum with a peak average energy that grows with time, for example, stepwise, and then repeats itself and can continue to cycle. The present invention also provides methods wherein elemental identification is achieved by time-correlating x-ray counts detected by the detector, with the time-variable applied radiation field. The system and method provide design flexibility for many commercial, and NASA, applications.

The present invention provides a new MXRF system and method that can identify resources and that exhibit design flexibility that is currently unavailable in existing XRF systems. The method enables high-speed mapping of resources at the scale of feet, meters, or better, without the need for the detector to be in close proximity to the sample. The system and method can be used on and with the undercarriage of a lunar rover or other vehicle for high-speed chemical characterization of terrain without the need for robotic arms or manipulators. The MXRF system and method of the invention work at great distances from the samples being analyzed, and when mounted on a vehicle, the great distances enable the system to be mounted to avoid damage by uneven terrain, rocks, boulders, or other obstacles. The system and method also work in analyzing very fast-moving samples. For example, the system and method can analyze ore from a mine speeding past the system on a conveyor belt, and so can expedite identification of mining resources. In addition, the system can be used for material identification for science objects to understand the origin of the moon and solar system. The design flexibility enabled by the present invention simplifies its implementation in future exploration systems.

BRIEF DESCRIPTION OF THE DRAWINGS

The present invention can be even more fully understood with reference to the accompanying drawings, which are intended to illustrate, not limit, the present invention.

DETAILED DESCRIPTION OF THE INVENTION

According to various embodiments of the present invention an x-ray fluorescence detection system is provided that comprises a plurality of different sources of ionizing radiation. In an exemplary embodiment, the system can comprise a first source of ionizing radiation that, when activated, provides low energy x-rays directed toward a sampling area. A second source of ionizing radiation can also be provided that, when activated, produces high energy x-rays directed toward the same sampling area. The high energy x-rays can be of higher energy than the low energy x-rays. A control unit can be included and configured to control activation of the first source of ionizing radiation and the second source of ionizing radiation, alternately and intermittently. The control unit can control the system such that the first source is activated during a time interval $T_1$ while the second source is not activated, and so that the second source is activated during a time interval $T_2$ while the first source is not activated. A detector can be provided spaced away from the sampling area and configured to detect fluoresced x-rays, for example, x-rays characteristic of atomic emission lines, produced by a sample in the sampling area upon excitation of atoms in the sample, caused by one or both of the low energy x-rays and the high energy x-rays. The control unit can be further configured to correlate a level of detection of the characteristic x-rays with the time intervals $T_1$ and $T_2$. In so doing the control unit can process the information and determine the characteristic binding energies and thus the atomic composition of the sample.

A sample can be located within the sampling area, for example, an iron-containing sample. The first source of ionizing radiation can comprise, for example, cobalt, or another element that would not produce x-rays of sufficient energy to exceed the threshold binding energy of the K shell of an iron atom. An electron-impact or other excitation source can be used to activate the cobalt to produce the low energy x-rays. For a sample suspected of containing iron, or to determine whether a sample contains iron, for example, the second source of ionizing radiation can comprise nickel and an electron-impact or other excitation source configured to activate the nickel to produce the high energy x-rays. Although just two sources are mentioned, it is to be understood that a plurality of additional sources of ionizing radiation can be used, each of which, when activated, can produce x-rays directed toward the sampling area and of a unique energy level. Each unique energy level can be different than the x-ray energy levels of the other additional sources, when respectively activated. Each unique energy level can also be different than the energy levels of the low energy x-rays and of the high energy x-rays.

According to various embodiments, the control unit can be configured to control activation of the first source and of the second source, alternately and intermittently, to start and stop the respective activations, for example, at regular intervals. The time intervals do not necessarily have to be regular intervals. A user may instead, for example, illuminate the sample with the low energy applied x-rays for longer intervals than the high-energy x-rays. The intervals can be established intervals, predetermined intervals, programmed intervals, or the like.

The first source of ionizing radiation and the second source of ionizing radiation can each comprise, for example, an ultraviolet emitter that emits ultraviolet light, a photocathode operably coupled to the ultraviolet emitter and that emits electrons, an electron multiplier operably coupled to the photocathode and that multiplies incident electrons, and an electron target (also referred to as an anode) operably coupled to the electron multiplier and that is configured to produce x-rays. Such sources can be, or use, components as described in U.S. Patent Application Publication No. US 2014/0044239 A1 to Gendreau et al., which is incorporated herein in its entirety by reference. In some cases, the ultraviolet emitter can comprise an ultraviolet light-emitting diode. The system can further comprise, for one or more, or each, ultraviolet emitter, a current driver configured to drive current to the respective ultraviolet emitter, and the control unit can be configured to modulate each of the first source of ionizing radiation, the second source of ionizing radiation, and any additional sources of ionizing radiation, by modulating the respective drive current to the respective ultraviolet emitter.

According to various embodiments of the present invention, a sample in the sampling area can be irradiated and detected from many inches away, for example, from at least one foot away, from at least three feet away, or from even further away. In some embodiments, the detector can comprise an enclosure containing a gas susceptible to ionization by x-rays, an electric field within the enclosure, and an enclosure opening fitted with a transparent material through which x-rays fluoresced by a sample in the sampling area can enter the electric field. The opening can be a large opening. The opening can be, for example, at least four square inches, at least 8 square inches, at least 10 square inches, at least 16 square inches, or larger. In a typical embodiment, the detector provides the times at which x-ray photons are detected, but has modest or no energy-dispersive capability. In some embodiments, the detector can comprise timing capability and can also comprise energy-dispersive capability.

According to various embodiments, the first and second sources of ionizing radiation can be mounted in or on a vehicle, for example, on a lunar rover or environmental monitoring vehicle, to search, for example, for chemical spills on roadways. The first and second sources of ionizing radiation can be mounted in or on a vehicle so as to direct the low energy x-rays and the high energy x-rays, respectively, downwardly from an underside of the vehicle. The detector can also be mounted on the underside of the vehicle and does not have to extend to ground level. Instead, the detector can be one foot, three feet, or even further away from the surface of the terrain being traversed by the vehicle. According to various embodiments, the sampling area can comprise a conveyor, such as a fast-moving conveyor belt. The detector can be spaced away from the conveyor and configured to detect x-rays fluoresced from a sample moving on the conveyor.

In yet other embodiments of the present invention, an x-ray fluorescence detection method is provided. The method can comprise activating a first source of ionizing radiation to produce low energy x-rays, directing the low energy x-rays toward a sample for a first time interval $T_1$, activating a second source of ionizing radiation to produce high energy x-rays, and directing the high energy x-rays toward the sample for a second time interval $T_2$ that does not overlap with the first time interval $T_1$. X-rays fluoresced by the sample, as a result of irradiation by the low energy x-rays and the high energy x-rays, can be detected during the time intervals $T_1$ and $T_2$. X-rays fluoresced, if any, during time interval $T_1$, can be compared to x-rays fluoresced, if any, during time interval $T_2$, and the relative binding energies of atoms in the sample can be determined based on the comparison of the quantity of x-rays fluoresced during the two different time intervals $T_1$ and $T_2$. The method can further comprise comparing the relative binding energies determined to known atomic binding energies of known atoms, and determining the atomic composition of the sample based on the comparison to known atomic binding energies. In some embodiments, the method can further comprise predicting a suspected atomic composition of a sample, selecting as the first source of ionizing radiation a source that produces low energy x-rays that do not exceed a threshold binding energy of atoms predicted to be in the sample, and selecting as the second source of ionizing radiation a source that produces high energy x-rays that exceed a threshold binding energy of atoms predicted to be in the sample. If characteristic x-rays are produced by a sample during time intervals of exposure to the high energy x-rays but not to the low energy x-rays, conclusions can reasonably be drawn as to the atomic composition of the sample.

In some embodiments, the method can further comprise separately activating and directing x-rays from a plurality of additional sources of ionizing radiation, each during a respective, different time interval that does not overlap with the time intervals during which the other sources of ionizing radiation are activated. The method can then entail detecting x-rays fluoresced, if any, during each respective time interval. Each additional source of ionizing radiation of the plurality can produce x-rays of a different energy level relative to the energy levels of x-rays produced by the first, second, or other additional sources of ionizing radiation, where the collection of source energy levels may be selected to ascertain, through stimulation of characteristic emission lines, the presence or absence of specific suspected atomic constituents within the sample.

The methods of the present invention can be used on vehicles, for example, such that the low energy x-rays are directed downwardly from an underside of the vehicle, the high energy x-rays are directed downwardly from the underside of the vehicle, and the detecting is carried out by a detector mounted on the underside of the vehicle. In some embodiments, the method can be used on a conveyor system, for example, such that the low energy x-rays are directed toward a conveyor, the high energy x-rays are directed toward the conveyor, and the detecting is carried out by a detector configured to receive x-rays fluoresced from a sample on the conveyor.

Figure 1:
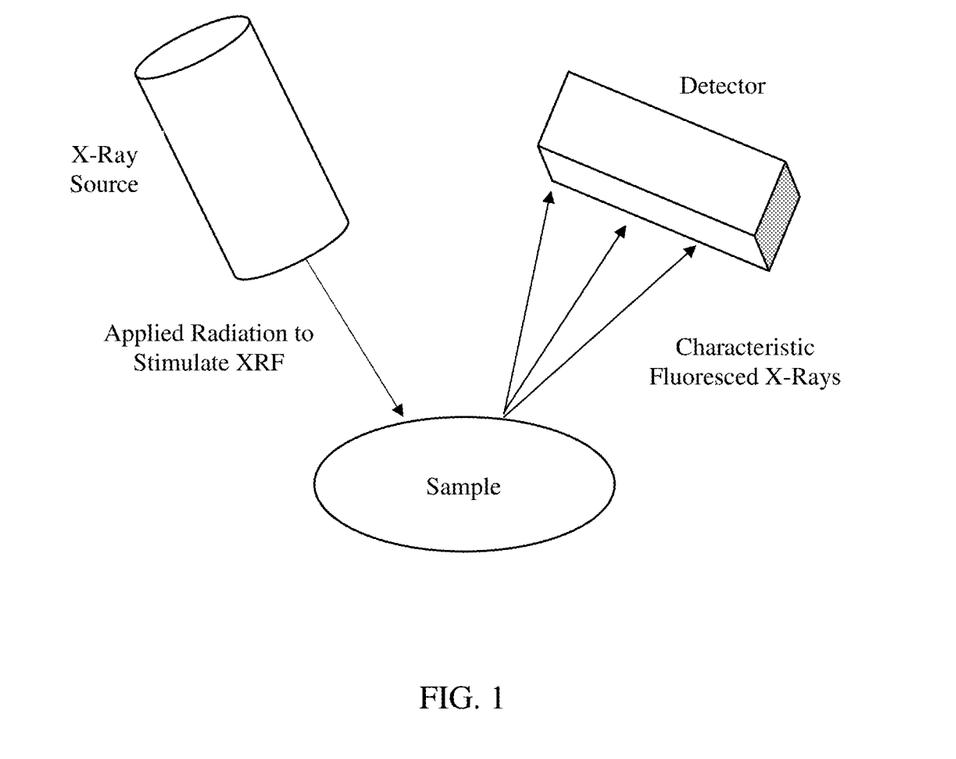
FIG. 1 is a schematic diagram showing basic components of an X-ray fluorescence measurement system according to the present invention.

The system and method of the present invention can be used to identify elements in a sample using the energy levels of the innermost bound electrons of the atoms that make up the elements. For example, the system and method can be used to identify materials found at crime scenes, extracted from mines, in pieces of ancient artwork, or on other planets. There are three basic components of the system, as shown in FIG. 1, a source of stimulating radiation (usually an x-ray source or radioisotope), the sample in question, and an x-ray detector. Additional components, for example, controlled shutters (not shown), can be used to control emission times of radioisotopes in the present MXRF systems.

Figure 2A:
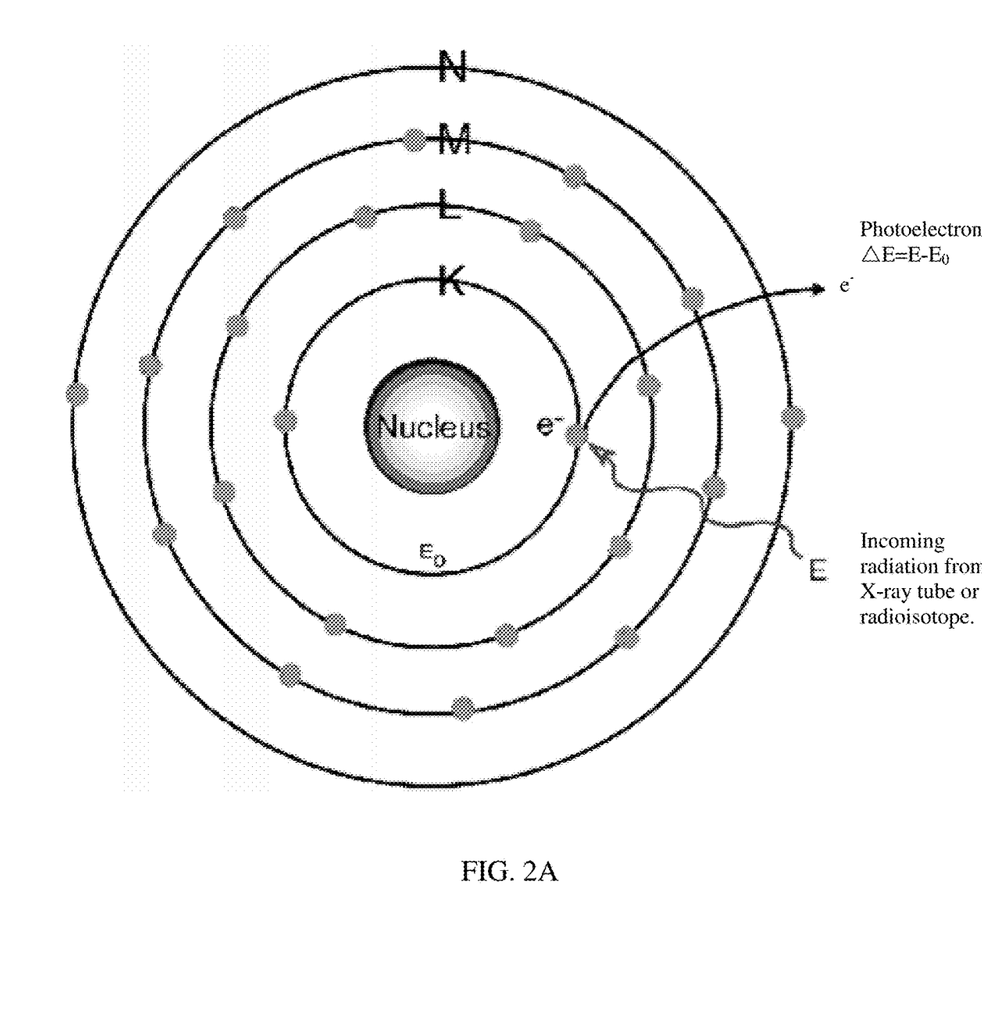
FIG. 2A is a schematic diagram showing ionization of an atom's innermost shell.
Figure 2B:
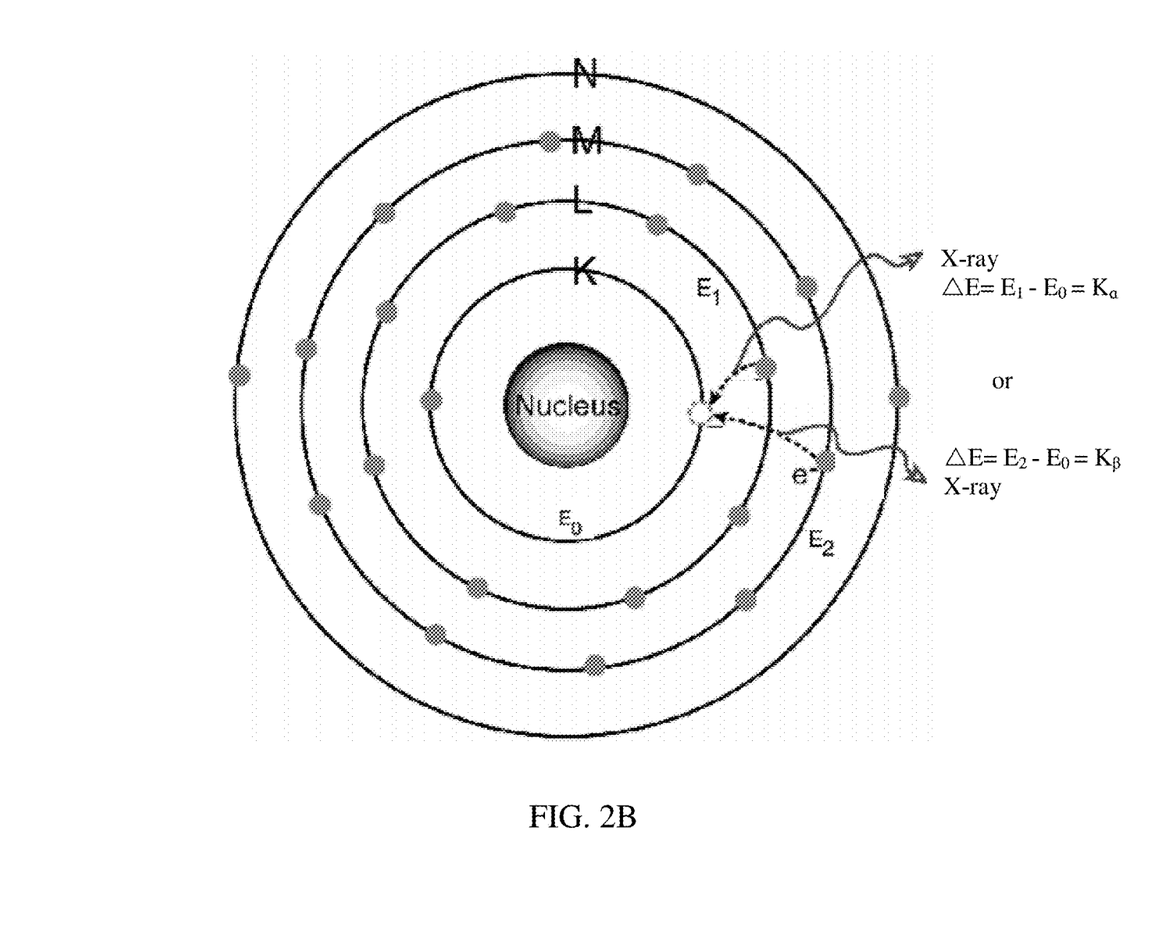
FIG. 2B is a schematic diagram showing emission of characteristic radiation by electrons transitioning from outer shells.
Figure 3:
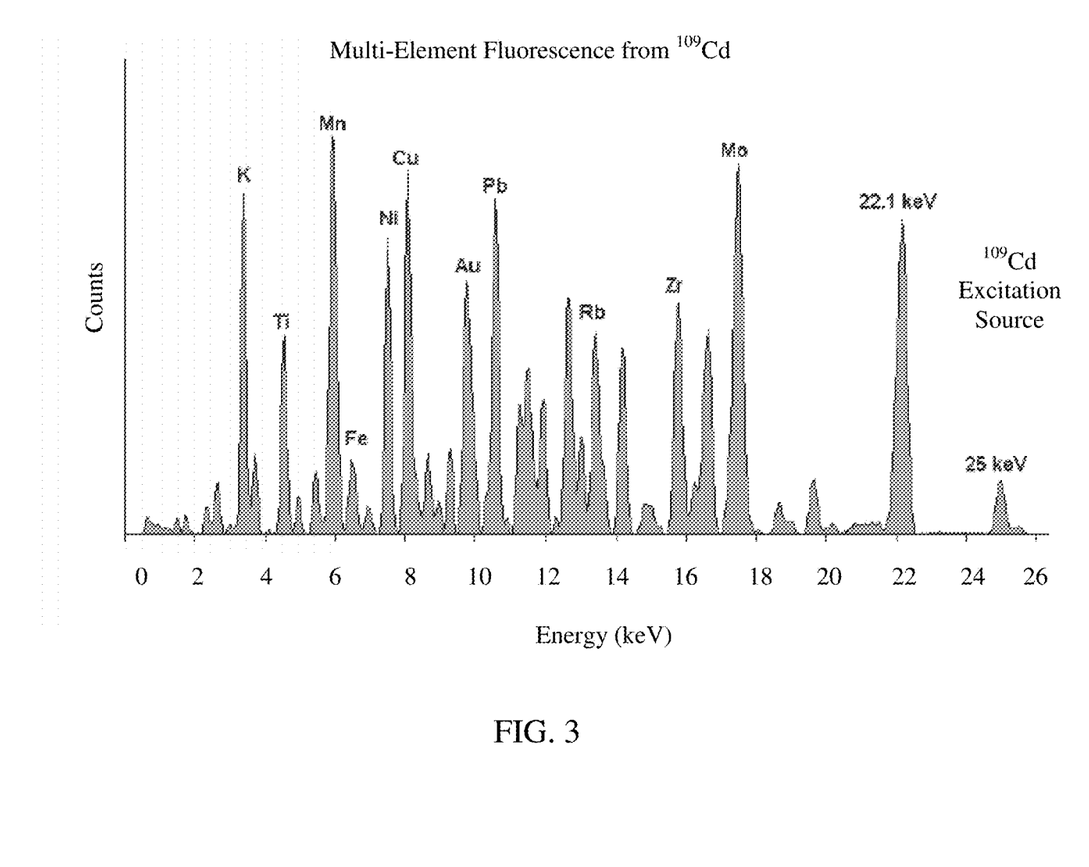
FIG. 3 is a typical XRF elemental analysis using an energy-dispersive (ED) detector.

The physics involved are exemplified in FIGS. 2A and 2B. The innermost electrons of atoms are bound to their nuclei by specific "binding energies." In the figure, K-shell electrons are held at an energy $E_0$, L-shell electrons are held at an energy $E_1$, and so on. These binding energies are specific to the type of atom, namely, to the chemical element typified by the atom. If the atom is exposed to ionizing radiation (either photons or particles) with energy greater than the binding energies, then there is a non-zero probability that an inner electron will absorb a quantum of the applied radiation. This electron will be ejected from the atom, which is now "ionized" with a vacancy where the sacrificed electron resided. Usually, this vacancy is filled by an electron held at a different binding energy, in an outer shell. When this outer shell electron falls into the inner shell vacancy, an X-ray photon is emitted with a well-defined energy equal to the difference between the two binding energies. This emitted photon is called a "characteristic x-ray." In traditional XRF, elemental identification is determined by measuring the energies of the emitted photons (spectroscopy) using an ED detector. FIG. 3 shows an example XRF spectrum obtained with a detector from Amptek, Inc. of Bedford, Mass. The present invention can capitalize on these specific binding energies of inner-shell electrons to select appropriate sources of ionizing radiation applied in a time-multiplexed fashion.

According to various embodiments, the MXRF of the present invention identifies elements by adjusting the energy of the applied radiation until it exceeds threshold binding energies of atoms within the sample, as illustrated in FIG. 2A. If the applied radiation energy is below the threshold, no ionization occurs and thus no characteristic x-rays are emitted. If the applied radiation energy is above the threshold, then ionization is enabled and usually followed by the emission of a characteristic x-ray.

According to the present invention, the detector does not require energy-dispersive capability because its output can be time-correlated with changing applied radiation. The detector can thus be of simple construction because it does not need energy resolution, and it can be made large. The detector can capture a large solid angle of the emitted radiation from a great distance because the detector can be physically large.

Figure 4A:
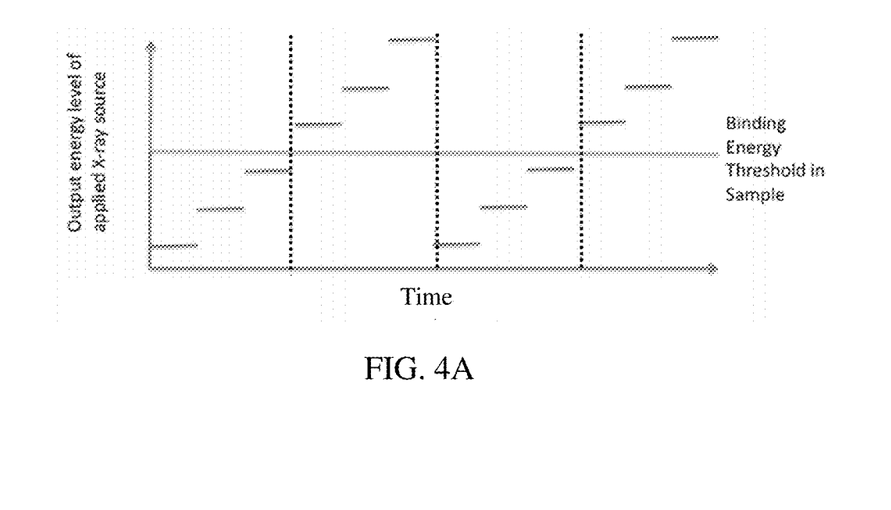
FIG. 4A is a schematic graph showing cycling energies of applied radiation over time, relative to the ionization threshold of a chemical element found in the sample, in accordance with an embodiment of the present invention.
Figure 4B:
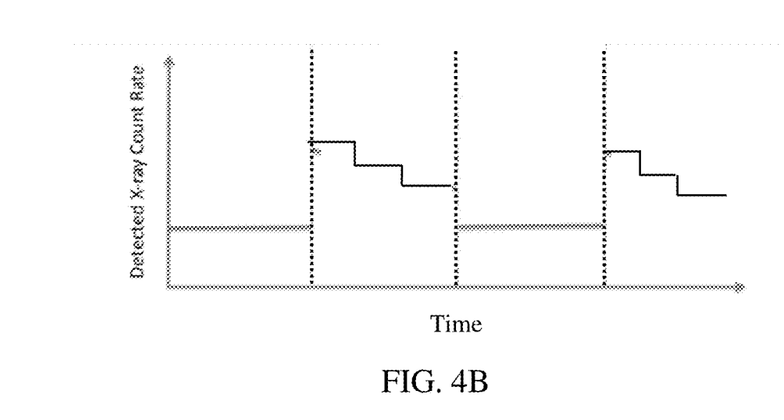
FIG. 4B is a schematic graph showing the photon count rate in a non-energy-dispersive detector resulting from the application of energy shown in FIG. 4A.

An x-ray source can be used as the applied radiation source. The x-ray source can be of an electron impact design that produces an output spectrum dependent on the acceleration energy of the electrons as well as on the target material. To adjust the energy of the applied radiation for the stimulation of XRF, the electron impact target material or accelerating potential can be rapidly adjusted or changed. Such a source produces x-rays with a spectrum that can have increasing energy levels with time, with a repeating cycle. Alternatively, a plurality of x-ray sources each producing output predominantly of a single energy can be multiplexed with time on a repeating cycle. FIGS. 4A and 4B show how the correlation of the detected x-ray counts with the time-dependent applied x-ray source output can yield an identification of an element.

By employing time-correlation between applied radiation and detected fluoresced x-rays, the present invention provides a system and method wherein XRF analysis is enabled for detectors, with modest or no ED capability, that are unsuitable for traditional XRF but which are advantageous for a variety of novel applications because they can be made very large and require only timing capability. In some embodiments the applied radiation is provided by one or more modulated x-ray sources (MXS) that can be switched on and off extremely quickly. The MXS can also be modified or changed to provide high speed switching of the energies it produces. The system and method of the present invention couple simple, large, low energy-resolution, and inexpensive x-ray detectors with multiplexing modulated x-ray sources (MMXS) to reveal elemental composition. Exemplary MMXS methods, systems, and sources that can be used in or as part of the present invention include those described in U.S. Patent Application Publication No. US 2014/0044239 A1, which is incorporated herein in its entirety by reference.

The MMXS floods a sample with x-rays generated with energies that change on command, in a pattern that is synchronized with x-ray data acquired by the detector. For example, the MMXS can produce low energy x-rays followed by progressively higher energy x-rays, and then recycle. As the MMXS x-ray energies exceed the characteristic absorption edges of the constituent elements of the sample, the sample will produce characteristic x-rays to which the detector will respond. By correlating the count rate produced by the detector with the known MMXS energies, the elemental composition of the sample can be determined without an expensive, small ED detector.

The MXRF detector can be made large and so it can be positioned or located further away from the sample than a typical small ED detector would need to be (mm), yet the detector of the present invention can still capture the same solid angle of emitted XRF photons. Variations of MXRF can be tuned to particular elements such as lead for detection of lead paint in old houses, tuned to identify a vein of titanium in rubble from iron ore extracted from a mine, tuned to identify layers of an exposed surface of a geological feature, or designed for a broad suite of elements for exploration purposes on the Moon or Mars.

Figure 5:
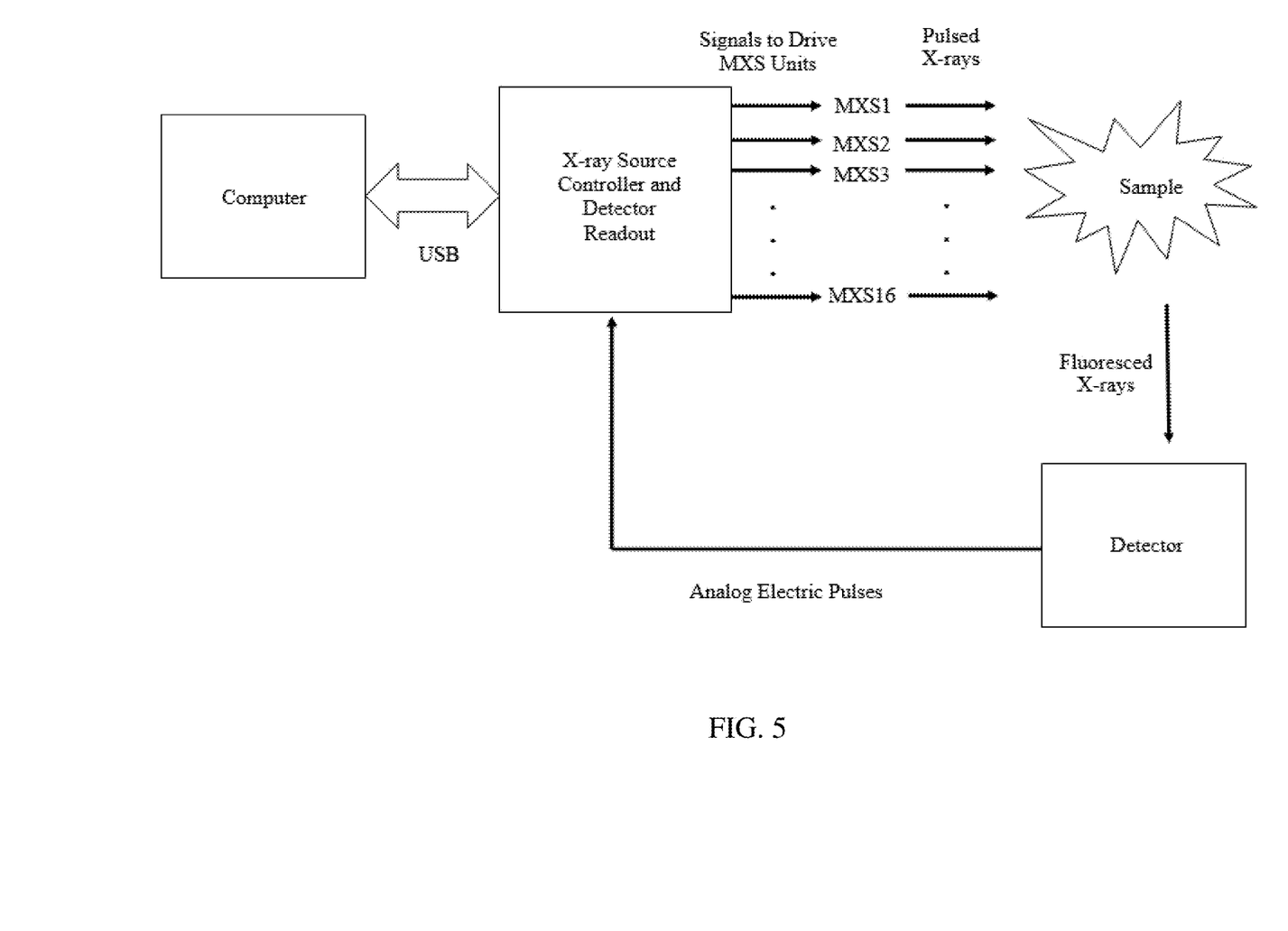
FIG. 5 is a block diagram of an MXRF system in accordance with an embodiment of the present invention.

According to one or more embodiments of the present invention, as shown in FIG. 5, a plurality of MXS is used to produce a time varying x-ray spectrum. The multiple MXS provide a high-speed switchable spectrum of x-rays with arbitrary intensity control. The detector can be a large area, inexpensive proportional counter. The one or more x-ray sources can be controlled, and the detector output recorded, together or independently, for example using a field-programmable gate array (FPGA) with connectivity to a computer and high-speed Analog to Digital Converters (ADCs), to coordinate the MXS operations and the readout of the detector. A computer can be used to accumulate data and provide analysis capability.

According to yet further embodiments of the present invention, the MXS can comprise an electron impact x-ray source. Electron impact sources produce x-rays by accelerating electrons to high energy and directing them onto targets. The spectrum of x-rays produced is a function of the acceleration energy and the nature of the target material. For example, electrons accelerated across a 10 kV potential onto titanium will produce a continuum spectrum peaking at approximately 6 keV from Bremmstrahlung "braking" radiation as well as characteristic x-ray emission from titanium. The total emitted spectrum is overwhelmingly dominated by the characteristic lines of titanium near 4.5 keV. In another example, two MXS units with electron targets of nickel (Ni) and cobalt (Co) can be used that yield spectra dominated by Ni K alpha (7.48 keV) and Co K alpha (6.93 keV). The MXS differs from usual electron impact sources in that its electrons are seeded by photoelectrons stimulated by optical light; typical electron impact x-ray sources use hot filaments to provide electrons. The photoelectrons of the MXS can be switched on and off much more rapidly than the thermally produced electrons of a hot filament. This allows for rapid x-ray transitions. UV LEDs can be used to stimulate the photoelectrons of the MXS. An FPGA-based or similar controller can rapidly modulate the LEDs, and thus the output of each MXS. Different LEDs can be used to drive the MXS units, for example, two units having targets of nickel and cobalt, respectively. The FPGA can thus control the spectral output of the combined MXS units by toggling between which LED is activated.

The detector can comprise an enclosure, for example, an aluminum box with a 4-inch diameter hole. The hole can be covered with aluminized mylar film that is transparent to x-rays higher in energy than approximately 3 keV. Inside the enclosure is a copper-topped electronics board mounted on top of a piece of aluminum backing to define an electric field for electron multiplication. The board can have dimensions of any size, for example, of about four inches by four inches. An exemplary electronics board that can be used is VECTORBORD® available from Vector Electronics & Technology, Inc., of North Hollywood, Calif. The top copper of the board can be held at approximately 100 volts compared to the enclosure body, to provide a drift field for electrons produced by x-ray interactions in P-10 gas filling the enclosure. As electrons from x-ray interactions in the P-10 gas drift toward the vector board, they feel the sudden acceleration from a 1.8 kV potential applied to the aluminum backing attached to the board. This acceleration produces a charge avalanche, which amplifies the charge clouds from the x-ray detections. These larger charge clouds are easily detected by charge-sensitive pre-amplifiers coupled to the detector, for example, those available from Cremat Inc., of West Newton, Mass.

The FPGA circuit that controls the MXS operations can also use high-speed ADCs to read out shaped pulses from the detector. Data is accumulated in the FPGA circuit into bins corresponding to the particular MXS LED that is being pulsed, providing a system that correlates the detector output with the MXS source spectra. A block diagram is shown in FIG. 5.

The MXS can be configured to produce multiple energies by including a source with several different electron targets and dedicated photocathodes as the electron sources. The electron targets can be micropatterned and can use electron focusing to control the output energy. A 10 cm square (100 cm$^2$) simple detector and electronics board can be used to record counts. A computer can be used to coordinate the MMXS and the detector.

Different types of modulated x-ray sources that modulate slowly but at an adequate rate for MXRF, can be simpler to implement. A hot filament electron impact x-ray source can be used and can easily produce copious flux to excite XRF. A mechanical system, as opposed to an electronic system, can be used to produce the applied radiation of different energies. Mechanical modulation can be implemented by using, for example, a ring of non-modulated x-ray sources, of different energies, behind a shutter wheel.

The system and method of the present invention make use of time-variable x-ray sources to eliminate the need for expensive energy dispersive detectors. The system and method can use very large simple and inexpensive x-ray counters to build an XRF system that can work at a distance and enable several material identification systems.

EXAMPLE

A test was carried out using a pair of MXS units. One unit produced primarily 6.93 keV (Co K alpha) radiation, and the other unit produced primarily 7.48 keV (Ni K alpha) radiation. For the samples, iron and chromium were used as two respective samples and a control "sample" had no material. The control was used to provide an estimate of background. Iron has a K binding edge energy of 7.11 keV, and thus would only be stimulated into XRF by the Ni (7.48 keV)

Figure 6:
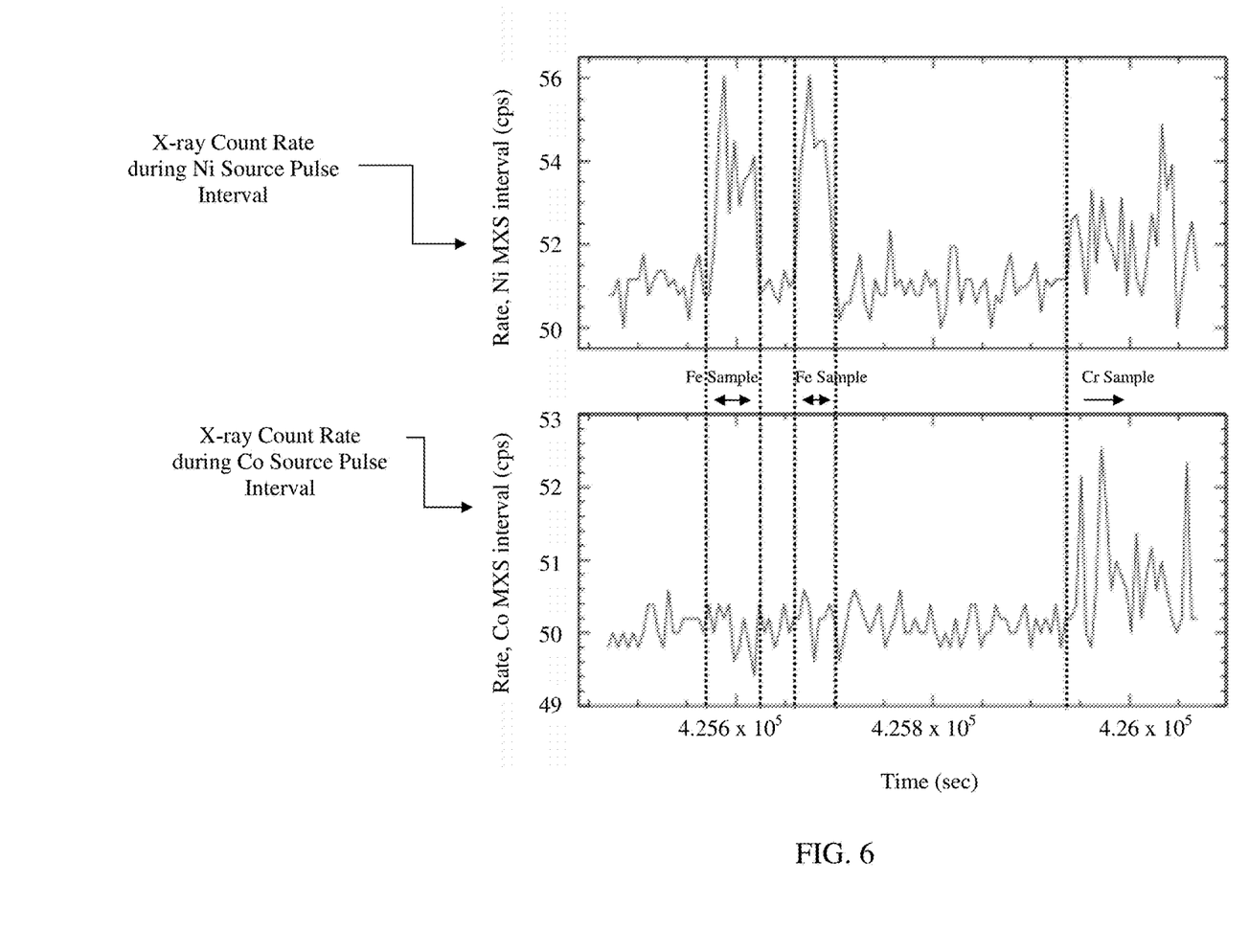
FIG. 6 is a graph demonstrating time-modulated x-ray fluorescence measurements of iron and chromium obtained from a system and method of the present invention.

MXS. Chromium has a binding energy of 5.99 keV and could be stimulated by both the Ni and Co MXS units. This MXS configuration and choice of samples produced the expected results, as shown in FIG. 6, representing a demonstration of the time-modulated x-ray fluorescence system and method of the present invention. The acronym "cps" in FIG. 6 is short for "counts per second."

The present invention can include any combination of the various features or embodiments described herein. Any combination of disclosed features herein is considered part of the present invention and no limitation is intended with respect to combinable features.

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether such ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to skilled artisans from consideration of the present specification and practice of the present invention disclosed herein. It is intended that the present specification and examples be considered as exemplary only with a true scope and spirit of the invention being indicated by the following claims and equivalents thereof.

What is claimed is:

1. An x-ray fluorescence detection system, the x-ray fluorescence detection system comprising:
    a first source of ionizing radiation that, when activated, provides low energy x-rays directed toward a sampling area;
    a second source of ionizing radiation that, when activated, produces high energy x-rays directed toward the sampling area, the high energy x-rays being of higher energy than the low energy x-rays;
    a control unit configured to control activation of the first source and of the second source, alternately and intermittently, so that the first source is activated during a time interval $T_1$ while the second source is not activated, and so that the second source is activated during a time interval $T_2$ while the first source is not activated; and
    a non-energy dispersive detector spaced away from the sampling area and configured to detect characteristic x-rays produced by a sample in the sampling area upon excitation of atoms in the sample, caused by one or both of the low energy x-rays and the high energy x-rays.

2. The x-ray fluorescence detection system of claim 1, the x-ray fluorescence detection system further comprising a processor, wherein the processor is configured to correlate a level of detection of the characteristic x-rays with the time intervals $T_1$ and $T_2$.

3. The x-ray fluorescence detection system of claim 2, wherein the control unit comprises the processor.

4. The x-ray fluorescence detection system of claim 1, the x-ray fluorescence detection system further comprising a plurality of additional sources of ionizing radiation, each of which, when activated, produces x-rays directed toward the sampling area and of a unique energy level that is different than the x-ray energy levels of the other additional sources of the plurality, when respectively activated, and that is different than the energy levels of the low energy x-rays and of the high energy x-rays.

5. The x-ray fluorescence detection system of claim 1, wherein the control unit is configured to control activation of the first source and of the second source, alternately and intermittently, to start and stop the respective activations at established intervals.

6. The x-ray fluorescence detection system of claim 1, wherein the first source of ionizing radiation and the second source of ionizing radiation each comprises:
    an ultraviolet emitter that emits ultraviolet light;
    a photocathode, operably coupled to the ultraviolet emitter, that emits electrons;
    an electron multiplier, operably coupled to the photocathode, that multiplies incident electrons; and
    an electron target, operably coupled to the electron multiplier, that is configured to produce x-rays.

7. The x-ray fluorescence detection system of claim 6, wherein the ultraviolet emitter is an ultraviolet light-emitting diode.

8. The x-ray fluorescence detection system of claim 6, the x-ray fluorescence detection system further comprising, for each ultraviolet emitter, a current driver configured to drive current to the respective ultraviolet emitter.

9. The x-ray fluorescence detection system of claim 8, wherein the control unit is further configured to modulate each of the first source of ionizing radiation and the second source of ionizing radiation by modulating the respective drive current to the respective ultraviolet emitter.

10. The x-ray fluorescence detection system of claim 1, the x-ray fluorescence detection system further comprising a sample in the sampling area, wherein the detector is spaced away from the sampling area by at least six inches.

11. The x-ray fluorescence detection system of claim 1, wherein the detector comprises an enclosure containing a gas susceptible to ionization by x-rays, an electric field within the enclosure, and an enclosure opening having an area of at least 10 square inches fitted with a transparent material through which x-rays fluoresced by a sample in the sampling area can enter the electric field.

12. The x-ray fluorescence detection system of claim 1, wherein the first and second sources of ionizing radiation are mounted in or on a vehicle so as to direct the low energy x-rays and the high energy x-rays, respectively, downwardly from an underside of the vehicle, and the detector is mounted on the underside of the vehicle.

13. The x-ray fluorescence detection system of claim 1, the x-ray fluorescence detection system further comprising a sampling area, the sampling area comprises a conveyor, and the detector is spaced away from the conveyor and configured to detect x-rays fluoresced from a sample moving on the conveyor.

14. An x-ray fluorescence detection method, the x-ray fluorescence detection method comprising:
    activating a first source of ionizing radiation to produce low energy x-rays;
    directing the low energy x-rays toward a sample for a first time interval $T_1$;
    activating a second source of ionizing radiation to produce high energy x-rays;
    directing the high energy x-rays toward the sample for a second time interval $T_2$ that does not overlap with the first time interval $T_1$;

with a non-energy dispersive detector, detecting x-rays fluoresced by the sample, as a result of irradiation by the low energy x-rays and the high energy x-rays, during the time intervals $T_1$ and $T_2$;

comparing x-rays fluoresced, if any, during time interval $T_1$, to x-rays fluoresced, if any, during time interval $T_2$; and determining relative binding energies of atoms in the sample, based on the comparison of the x-rays fluoresced during the two different time intervals $T_1$ and $T_2$.

15. The method of claim 14, the method further comprising:

comparing the relative binding energies determined, to known atomic binding energies of known atoms; and determining the atomic composition of the sample based on the comparison to known atomic binding energies.

16. The method of claim 14, the method further comprising:

predicting the atomic composition of a sample;

selecting as the first source of ionizing radiation a source that produces low energy x-rays that do not exceed a threshold binding energy of atoms predicted to be in the sample; and selecting as the second source of ionizing radiation a source that produces high energy x-rays that exceed a threshold binding energy of atoms predicted to be in the sample.

17. The method of claim 14, the method further comprising separately activating and directing x-rays from a plurality of additional sources of ionizing radiation, each during a respective, different time interval that does not overlap with the time intervals during which the other sources of ionizing radiation are activated, and detecting x-rays fluoresced, if any, during each respective time interval, wherein each additional source of ionizing radiation of the plurality produces x-rays of a different energy relative to the energies of x-rays produced by the first, second, or other additional sources of ionizing radiation.

18. The method of claim 14, wherein the sample is spaced away from the non-energy dispersive detector by at least six inches.

19. The method of claim 14, wherein the low energy x-rays are directed downwardly from an underside of a vehicle, the high energy x-rays are directed downwardly from the underside of the vehicle, and the detecting is carried out by the non-energy dispersive detector mounted on the underside of the vehicle.

20. The method of claim 14, wherein the low energy x-rays are directed toward a conveyor, the high energy x-rays are directed toward the conveyor, and the detecting is carried out by the non-energy dispersive detector configured to receive x-rays fluoresced from a sample on the conveyor.

* * * * *